US008311631B2

(12) United States Patent  
Hopper et al.

(10) Patent No.: US 8,311,631 B2
(45) Date of Patent: Nov. 13, 2012

(54) SYSTEMS AND METHODS FOR IMPROVING HEART RATE KINETICS IN HEART FAILURE PATIENTS

(75) Inventors: Donald Hopper, Maple Grove, MN (US); Yinghong Yu, Shoreview, MN (US); Yanting Dong, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 596 days.

(21) Appl. No.: 12/545,676

(22) Filed: Aug. 21, 2009

(65) Prior Publication Data

US 2009/0312815 A1 Dec. 17, 2009

Related U.S. Application Data

(62) Division of application No. 11/478,015, filed on Jun. 29, 2006, now Pat. No. 7,599,741.

(51) Int. Cl.
  *A61N 1/365* (2006.01)
(52) U.S. Cl. ............... 607/19; 607/9; 607/17; 607/18; 607/20
(58) Field of Classification Search ............... 600/520; 607/9, 11, 17–26
  See application file for complete search history.

(56) References Cited

U.S. PATENT DOCUMENTS

| 4,562,841 | A |   | 1/1986 | Brockway et al. |
| 4,884,576 | A | * | 12/1989 | Alt ............... 607/18 |
| 4,928,688 | A |   | 5/1990 | Mower |
| 5,036,849 | A |   | 8/1991 | Hauck et al. |
| 5,133,353 | A |   | 7/1992 | Hauser |
| 5,179,945 | A |   | 1/1993 | Van Hofwegen et al. |
| 5,203,348 | A |   | 4/1993 | Dahl et al. |
| 5,230,337 | A |   | 7/1993 | Dahl et al. |
| 5,284,136 | A |   | 2/1994 | Hauck et al. |
| 5,313,953 | A |   | 5/1994 | Yomtov et al. |
| 5,314,459 | A |   | 5/1994 | Swanson et al. |
| 5,318,597 | A |   | 6/1994 | Hauck et al. |
| 5,334,222 | A |   | 8/1994 | Salo et al. |
| 5,360,442 | A |   | 11/1994 | Dahl et al. |
| 5,366,496 | A |   | 11/1994 | Dahl et al. |
| 5,376,106 | A |   | 12/1994 | Stahmann et al. |
| 5,388,578 | A |   | 2/1995 | Yomtov et al. |
| 5,391,200 | A |   | 2/1995 | Kenknight et al. |
| 5,397,342 | A |   | 3/1995 | Heil, Jr. et al. |

(Continued)

OTHER PUBLICATIONS

Notice of Allowance dated May 29, 2009 from U.S. Appl. No. 11/478,015, 6 pages.

(Continued)

*Primary Examiner* — Carl H Layno
*Assistant Examiner* — Jennifer Ghand
(74) *Attorney, Agent, or Firm* — Hollingsworth Davis, LLC

(57) ABSTRACT

Adaptive rate pacing for improving heart rate kinetics in heart failure patients involves determining onset and sustaining of patient activity. The patient's heart rate response to the sustained activity is evaluated during a time window defined between onset of the activity and a steady-state exercise level. If the patient's heart rate response to the sustained activity is determined to be slow, a pacing therapy is delivered at a rate greater than the patient's intrinsic heart rate based on a profile of the patient's heart rate response to varying workloads. If determined not to be slow, the pacing therapy is withheld. Monitoring-only configurations provide for acquisition and organization of physiological data for heart failure patients. These data can be acquired on a per-patient basis and used to assess the HF status of the patient.

20 Claims, 7 Drawing Sheets

U.S. PATENT DOCUMENTS

| | | | |
|---|---|---|---|
| 5,411,031 | A | 5/1995 | Yomtov |
| 5,540,727 | A | 7/1996 | Tockman et al. |
| 5,545,202 | A | 8/1996 | Dahl et al. |
| 5,603,732 | A | 2/1997 | Dahl et al. |
| 5,620,466 | A | 4/1997 | Haefner et al. |
| 5,626,622 | A | 5/1997 | Cooper |
| 5,662,688 | A | 9/1997 | Haefner et al. |
| 5,836,987 | A | 11/1998 | Baumann et al. |
| 5,916,243 | A | 6/1999 | KenKnight et al. |
| 6,026,320 | A | 2/2000 | Carlson et al. |
| 6,044,298 | A | 3/2000 | Salo et al. |
| 6,055,454 | A | 4/2000 | Heemels |
| 6,190,324 | B1 | 2/2001 | Kieval et al. |
| 6,221,011 | B1 | 4/2001 | Bardy |
| 6,270,457 | B1 | 8/2001 | Bardy |
| 6,273,856 | B1 | 8/2001 | Sun et al. |
| 6,275,727 | B1 | 8/2001 | Hopper et al. |
| 6,277,072 | B1 | 8/2001 | Bardy |
| 6,280,380 | B1 | 8/2001 | Bardy |
| 6,285,907 | B1 | 9/2001 | Kramer et al. |
| 6,312,378 | B1 | 11/2001 | Bardy |
| 6,336,903 | B1 | 1/2002 | Bardy |
| 6,351,673 | B1 | 2/2002 | Ding et al. |
| 6,358,203 | B2 | 3/2002 | Bardy |
| 6,360,127 | B1 | 3/2002 | Ding et al. |
| 6,368,284 | B1 | 4/2002 | Bardy |
| 6,371,922 | B1 | 4/2002 | Baumann et al. |
| 6,398,728 | B1 | 6/2002 | Bardy |
| 6,405,085 | B1 | 6/2002 | Graupner et al. |
| 6,411,848 | B2 | 6/2002 | Kramer et al. |
| 6,411,850 | B1 | 6/2002 | Kay et al. |
| 6,424,865 | B1 | 7/2002 | Ding |
| 6,440,066 | B1 | 8/2002 | Bardy |
| 6,459,929 | B1 | 10/2002 | Hopper et al. |
| 6,463,325 | B1 | 10/2002 | Bolz |
| 6,490,485 | B1 | 12/2002 | Sun et al. |
| 6,542,775 | B2 | 4/2003 | Ding et al. |
| 6,597,951 | B2 | 7/2003 | Kramer et al. |
| 6,823,214 | B1 | 11/2004 | Sun et al. |
| 6,839,593 | B1 | 1/2005 | Sun et al. |
| 7,016,730 | B2 | 3/2006 | Ternes |
| 7,260,432 | B2 | 8/2007 | Kramer |
| 7,499,750 | B2 | 3/2009 | Haefner et al. |
| 2002/0120311 | A1 | 8/2002 | Lindh et al. |
| 2002/0143264 | A1 | 10/2002 | Ding et al. |
| 2004/0015195 | A1 | 1/2004 | Daum et al. |
| 2004/0098060 | A1 | 5/2004 | Ternes |
| 2004/0230230 | A1 | 11/2004 | Lindstrom |
| 2005/0137632 | A1 | 6/2005 | Ding et al. |
| 2006/0030892 | A1 | 2/2006 | Kadhiresan et al. |
| 2006/0036290 | A1 | 2/2006 | Hopper et al. |

OTHER PUBLICATIONS

Office Action Response dated Mar. 10, 2009 from U.S. Appl. No. 11/478,015, 7 pages.

Office Action dated Nov. 12, 2008 from U.S. Appl. No. 11/478,015, 18 pages.

B. Mettauer, Q. Zhao, et al., VO2 kinetics reveal a central limitation at the onset of subthreshold exercise in heart transplant recipients. J Applied Physiology 88:1228-1238, 2000.

Office Action dated Nov. 12, 2008 from priority U.S. Appl. No. 11/478,015.

\* cited by examiner

SYSTEMS AND METHODS FOR IMPROVING HEART RATE KINETICS IN HEART FAILURE PATIENTS

RELATED APPLICATIONS

This application is a division of 11/478,015, filed Jun. 26, 2006, now U.S. Pat. No. 7,599,741 to which Applicant claims priority under 35 U.S.C. §120, and which is incorporated herein by reference.

FIELD OF THE INVENTION

The present invention relates generally to monitoring and treating heart failure patients that suffer from delayed oxygen kinetics during the onset to activities.

BACKGROUND OF THE INVENTION

It is known that the heart's natural pacemaker (i.e., the sinus node) for many cardiac patients, particularly heart failure patients, provides an adequate heart rate for producing a cardiac output satisfactory for low levels of exertion, but not for high levels of exertion. This is known as chronotropic incompetence. Adaptive rate pacing has, in the past, been applied to patients to improve the chronotropic response to activities.

Rate responsive pacemakers have been developed that incorporate multiple sensors for measuring physiologic demand and for developing a control signal for delivering adaptive rate pacing under appropriate circumstances. For example, rate responsive pacemakers may incorporate an accelerometer for detecting patient movement and a minute ventilation sensor for detecting respiratory activity as an indicator of physiologic demand. When a patient having such a pacemaker implanted goes from a resting state to a minimal level of activity, the accelerometer will respond to the patient's stepping rate and the minute ventilation sensor will respond to the increased metabolic demand resulting in an increased paced heart rate from one or both of the sensors.

The physiologic sensors of rate responsive pacemakers provide inputs to a microprocessor-based controller for adjusting the rate at which cardiac pacing pulses are delivered to meet physiologic demand. It is difficult to predict an appropriate pacing function capable of generating a paced rate corresponding to a patient's metabolic demand at the time of implanting the pacemaker in the patient. Notwithstanding the efficacy of conventional rate responsive pacemakers, adjustments to the pacing rate by the microprocessor-based controller are made using a response factor that is based on estimated activity levels and target heart rates. Inappropriately computing or adjusting the response factor may result in a paced rate that is too high or too low for a given metabolic demand. If the paced rate is too high, the patient may feel palpitated or stressed. If too low, the patient may feel fatigued, tired or dizzy.

SUMMARY OF THE INVENTION

The present invention is directed to systems and methods for adaptively pacing a heart failure patient in response to the onset of patient activity. Adaptive pacing according to embodiments of the present invention is implemented to improve the mean heart rate response to the onset of exercise or activity of heart failure patients, resulting in improved oxygen kinetics and reducing the dependency on anaerobic metabolism.

The present invention is also directed to systems and methods for collecting, organizing, and analyzing data collected from heart failure patients. These data can be acquired on a per-patient basis and used to assess the HF status of the patient and to develop a physiologic profile for the patient. These data can also be used during adaptive rate pacing to improve heart rate kinetics in heart failure patients in the context of embodiments that provide for cardiac pacing therapies.

In accordance with embodiments of the present invention, methods for adaptively pacing a heart failure patient involve determining onset of patient activity and sustaining of the patient activity. Such methods further involve determining, for a time window defined between onset of the activity and a steady-state exercise level, whether the patient's heart rate response to the sustained activity is slow relative to an activity level of the patient. If the patient's heart rate response to the sustained activity is determined to be slow, a pacing therapy is delivered at a rate greater than the patient's intrinsic heart rate based on a profile of the patient's heart rate response to varying workloads. If the patient's heart rate response to the sustained activity is determined not to be slow, the pacing therapy is withheld.

Determining whether or not the patient is engaged in a sustained activity may involve sensing that the patient has been active for a time duration exceeding a threshold ranging between about 30 seconds and about 6 minutes. Determining whether or not the patient is engaged in a sustained activity may involve determining that the patient's stroke volume has reached a steady-state value in response to the patient activity.

The pacing therapy is delivered at a rate sufficient to increase the patient's heart rate response for reaching the steady-state exercise level of the sustained activity. In general, the pacing therapy is delivered at a rate sufficient to improve a chronotropic response of the patient to the sustained activity. Delivering the pacing therapy typically comprises adjusting an AV delay and/or VV delay parameter of the pacing therapy. An upper rate limit of the pacing therapy may be adjusted based on the patient's profile.

The patient profile may include one or both of the patient's intrinsic heart rate and minute ventilation at varying activity levels. The patient profile may include the patient's mean heart rate response time at varying activity levels. The patient's profile may be developed using an implantable medical device during a learning procedure. The learning procedure may involve acquiring one or more of heart rate, minute ventilation, and mean heart rate response time for the patient at varying activity levels. In one embodiment, the patient profile comprises a heart rate and a minute ventilation associated with each of a number of activity level ranges, and slowness of the patient's heart rate response is determined based on heart rate and minute ventilation values established for an activity level range of the profile corresponding to the patient's actual activity level.

In accordance with other embodiments of the present invention, an implantable cardiac device may include a number of electrodes positionable relative to a patient's heart, an activity sensor configured to detect activity of the patient, and a physiologic sensor configured to measure physiologic demand of the patient. A memory may be configured to store patient profile data. The patient profile data preferably includes heart rate and heart rate response data relative to varying workloads established for the patient.

A processor is coupled to the electrodes, activity sensor, physiologic sensor, and memory. The processor is configured to determine onset of patient activity and sustaining of the patient activity as measured by the activity sensor. The processor is further configured to determine whether the patient's heart rate response to the sustained activity as measured by the physiologic sensor is slow relative to an activity level of the patient during a time window defined between onset of the activity and a steady-state exercise level. The processor is also configured to deliver a pacing therapy at a rate greater than the patient's intrinsic heart rate based on the patient profile data if the patient's heart rate response to the sustained activity is determined to be slow. The processor is preferably configured to withhold the pacing therapy in response to the processor determining that the patient's heart rate response to the sustained activity is not slow.

The processor may be configured to determine sustaining of the patient activity in response to sensing an output signal produced by the activity sensor indicative of sustained patient activity for a time duration exceeding a threshold ranging between about 30 seconds and about 6 minutes. The processor may be configured to determine sustaining of the patient activity in response the patient's stroke volume reaching a steady-state value in response to the activity. The processor may be configured to determine sustaining of the patient activity in response to sensing an output signal produced by the activity sensor and the physiologic sensor, respectively.

The activity sensor may include an accelerometer or other rate sensor. The physiologic sensor may include a minute ventilation sensor or a pressure sensor.

The processor may be configured to adjust an upper rate limit of the pacing therapy based on the patient's profile. The processor may be configured to adjust an AV delay and/or VV delay parameter of the pacing therapy.

The processor may be configured to acquire patient profile data comprising one or both of the patient's intrinsic heart rate and minute ventilation. The processor may be configured to acquire patient profile data comprising mean heart rate response time data at varying activity levels. The patient profile data is preferably stored in the memory of the device. The processor may determine slowness of the patient's heart rate response based on patient profile data associated with an activity level of the profile corresponding to the patient's actual activity level.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
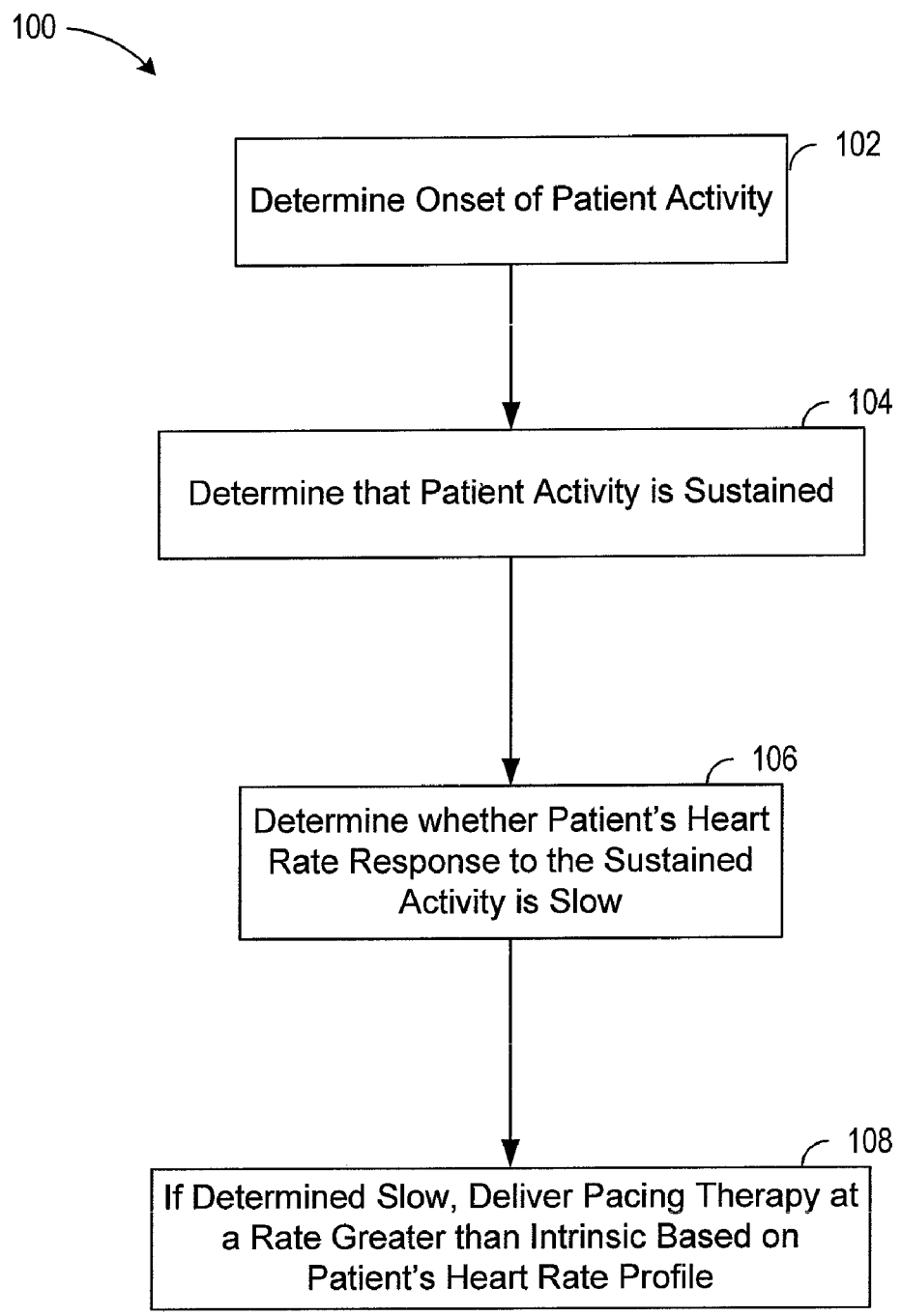
FIG. 1 is a flow diagram of a method for reducing a patient's mean heart rate response to the onset of activity in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

Detailed Description of Various Embodiments

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A medical device according to the present invention may include one or more of the features, structures, methods, or combinations thereof described hereinbelow. For example, a cardiac monitor, cardiac stimulator, or other type of implantable or patient-external medical device may be implemented to include one or more of the advantageous features and/or processes described below. It is intended that such a monitor, stimulator, or other external, implanted or partially implanted device need not include all of the features described herein, but may be implemented to include selected features that provide for useful structures and/or functionality. Such a device may be implemented to provide a variety of therapeutic or diagnostic functions.

A wide variety of implantable medical devices, such as cardiac monitoring and/or stimulation devices, may be configured to implement an adaptive rate pacing methodology and a patient profiling methodology of the present invention. A non-limiting, representative list of such devices includes cardiac monitors, pacemakers, cardiovertors, defibrillators, resynchronizers, and other cardiac sensing and therapy delivery devices. Such devices are referred to herein generally as a patient-implantable medical device (PIMD) for convenience.

The present invention is directed to systems and methods for improving heart rate kinetics in heart failure (HF) patients. Embodiments of the present invention are directed to reducing the time of the heart rate kinetics to steady-state activity. Embodiments of the present invention are also directed to improving the chronotropic response of a heart failure patient to activity and reducing their dependency on anaerobic metabolism.

The present invention is also directed to systems and methods for collecting, organizing, and analyzing data collected from heart failure patients. These data can be acquired on a per-patient basis and used to assess the HF status of the patient. These data can also be used during adaptive rate pacing to improve heart rate kinetics in heart failure patients.

During the onset to activities, heart failure patients demonstrate a delay in oxygen and heart rate kinetics, resulting in a higher dependency on anaerobic metabolism and a higher possibility of early termination of activities, such a exercise. One of the primary reasons for the delay to steady-state oxygen consumption is a reduced mean heart rate response to the onset of exercise. Reduced oxygen kinetics in heart failure patients is exemplified by a slower than normal heart rate response during the kinetic phase. A delayed rise in peak oxygen consumption in response to exercise may be responsible for subnormal values of peak oxygen consumption early in exercise in heart failure patients.

The mean response time of the heart rate kinetics to steady state can be determined via a time constant. For example, the heart rate mean response time may determined as follows:

$$HR_{MRT} = \frac{HR_{SS} - HR_{SE}}{CHR}$$

where $HR_{MRT}$ is the heart rate mean response time, $HR_{SS}$ is the heart rate at steady state exercise, $HR_{SE}$ is the heart rate deficit at the start of exercise, and CHR is the change in heart rate.

The delayed time to steady-state exercise determined during the early phase of exercise reflects a delayed cardiac output response in patients with severely impaired left ventricular function. The time to steady-state exercise is a sensitive and discriminate measure of impaired cardiac reserve. Data acquired during the kinetic phase may be used to assess the HF status of a given patient, and subsequently used as a basis for making adjustments to an adaptive rate pacing therapy delivered to the patient during the kinetic phase.

According to embodiments of the present invention, devices and methods of the present invention are directed to improving oxygen kinetics in heart failure patients by reducing the time to steady-state based on measuring the intrinsic heart rate to steady-state of an activity. Once the start of an activity has been declared and the activity has been sustained for a meaningful period of time, the patient's intrinsic heart rate response is measured in terms of time to steady-state during the period of activity. If the heart rate response is determined to be slow in relation to the activity level, then an adaptive rate pacing therapy is delivered to reduce the time of heart rate response to the activity. By using a combination of different sensors, heart rate specific to different activity levels can be measured to improve a patient's chronotropic response at different levels of activity, reducing the chance of over-pacing the heart failure patient.

Monitoring intrinsic heart rates and classifying activity levels by true activity events (e.g., sustained activity events), as well as measuring heart rate kinetics to the onset of activities, can be combined with profiling of the patient's heart rate to specific workloads to allow for custom tailoring of paced rates as compared to the current standard of adaptive rate pacing. For example, therapies for increasing heart rate kinetics to the onset of activity in heart failure patients may be programmable with respect to the rate of increased pacing rate for the activity. In addition, the patient's own intrinsic heart rate is preferably used as a target for the appropriate heart rate for the activity. The device may also be programmed as to specified paced heart rates that are not to be exceeded for specific activities.

Turning now to FIG. 1, there is illustrated a method 100 for reducing a patient's mean heart rate response to the onset of activity in accordance with embodiments of the present invention. According to the method 100 shown in FIG. 1, the onset of patient activity, such as exercise, is determined 102. A determination is made 104 as to whether or not the patient activity is sustained. For example, the determination 104 typically involves determining that the activity has been sustained for a period of time that is reflective of a steady-state activity.

If it is determined that the patient activity is sustained, a determination is made 106 as to whether or not the patient's heart rate response to the sustained activity is slow. For example, the patient's intrinsic heart rate response may be measured and evaluated as to the kinetic response of the patient's heart rate to the activity. If the patient's heart rate response to the activity is determined to be slow, a pacing therapy is delivered 108 to the patient at a rate greater than the patient's intrinsic heart rate. The pacing therapy is typically an adaptive rate pacing therapy.

This pacing therapy is preferably adjusted based on a heart rate response profile developed for the patient. For example, the pacing therapy may utilize the patient's own intrinsic heart rate-to-minute ventilation slope as a baseline measure to apply adaptive rate pacing during the exercise onset period.

Once the patient reaches steady-state activity, the patient's own intrinsic rate for the given workload is used to make adjustments to the pacing therapy, such as by governing upper rate pacing in order to reduce the chance of over-pacing the patient. In addition, the AV delay of the pacing therapy may be adjusted when adaptively adjusting the pacing rate during the exercise onset period (i.e., the kinetic phase). In general, the AV delay is typically extended out, within a range of 0-120 ms.

The minute ventilation response to the steady state exercise can be monitored to allow for a change in the sensed AV delay as well as in the paced AV delay. For a given level of work, the AV delay can be automatically adapted to result in a lower minute ventilation response to the level of work. Automatically adjusting or optimizing the AV delay and/or VV delay parameters in the context of the present invention may be implemented in a manner disclosed in commonly owned, U.S. Pat. Nos. 6,351,673, 7,123,960 and 7,181,285 all of which are hereby incorporated herein by reference.

Figure 2:
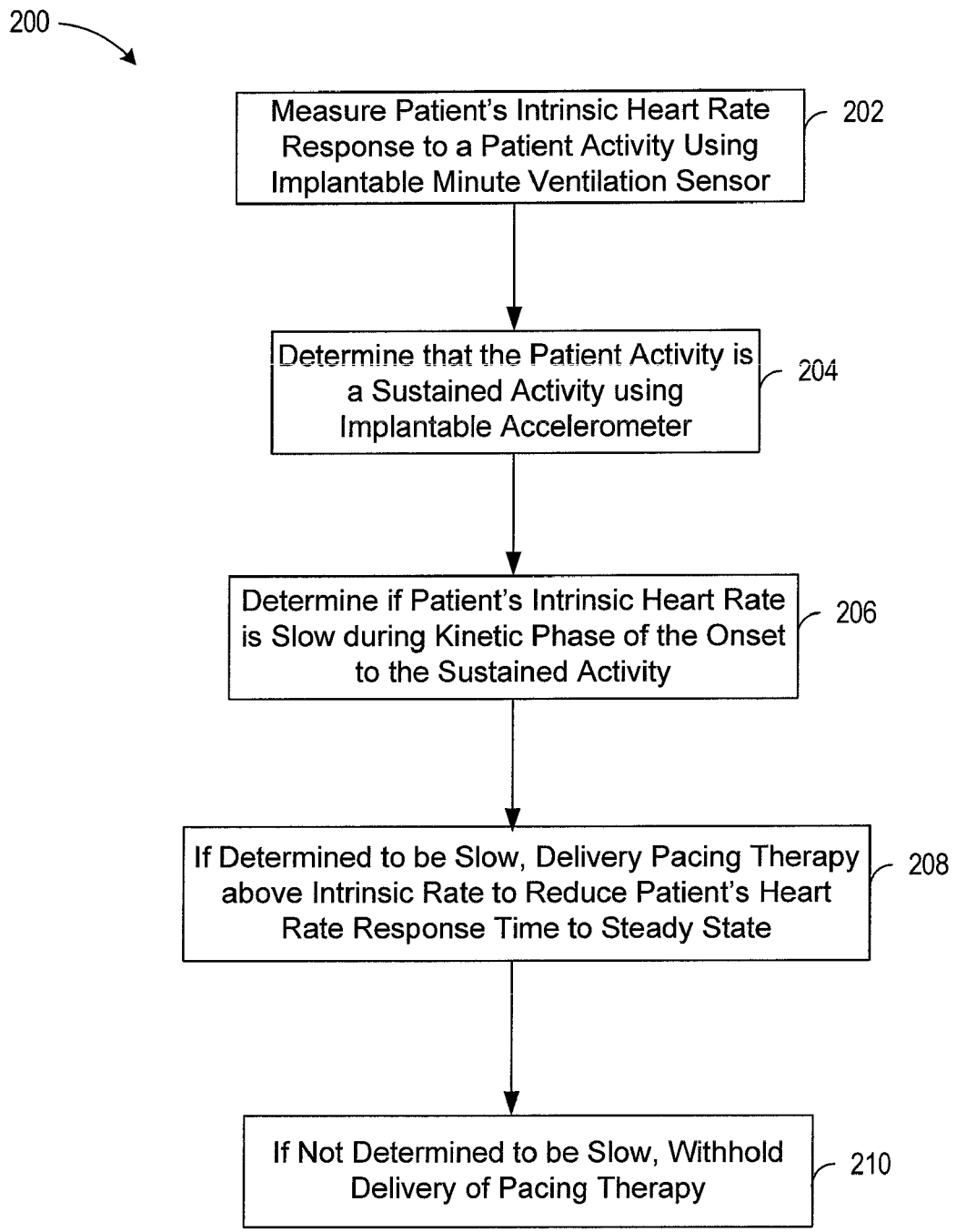
FIG. 2 is a flow diagram of a method for reducing a patient's mean heart rate response to the onset of activity in accordance with other embodiments of the present invention.

In FIG. 2, there is illustrated a method 200 of reducing a patient's mean heart rate response to the onset of activity in accordance with embodiments of the present invention. According to the method 200 shown in FIG. 2, a patient's intrinsic heart rate response to a patient activity is measured 202, such as by use of an implantable minute ventilation sensor or pressure sensor of a known configuration. The patient's activity is measured, such as by use of an implantable accelerometer of a known configuration. An output signal produced by the accelerometer is evaluated to determine 204 whether or not the patient is engaged in a sustained activity. Patient activity and sustaining of same as measured by the accelerometer may be confirmed using the minute ventilation sensor or pressure sensor. A valid activity event may be determined when the respective output signals of the accelerometer and minute ventilation or pressure sensors are in agreement that the patient is indeed engaged in a sustained activity.

If the patient in engaged in a sustained activity, a determination is made 206 as to whether or not the patient's intrinsic heart rate is slow during the kinetic phase of the onset to the sustained activity. If the patient's intrinsic heart rate during the kinetic phase of the onset to the sustained activity determined to be slow, a pacing therapy is delivered 208 above the patient's intrinsic heart rate in a manner that reduces the patient's heart rate response time to steady-state. In general, the pacing therapy is delivered at a rate sufficient to improve a chronotropic response of the patient to the sustained activity, without overpacing the patient.

If the patient's intrinsic heart rate during the kinetic phase of the onset to the sustained activity not determined to be slow, a pacing therapy is withheld 210. In this regard, energy associated with adaptive rate pacing therapy that may otherwise be expended in accordance with a conventional adaptive rate pacing approach is conserved.

Figure 3:
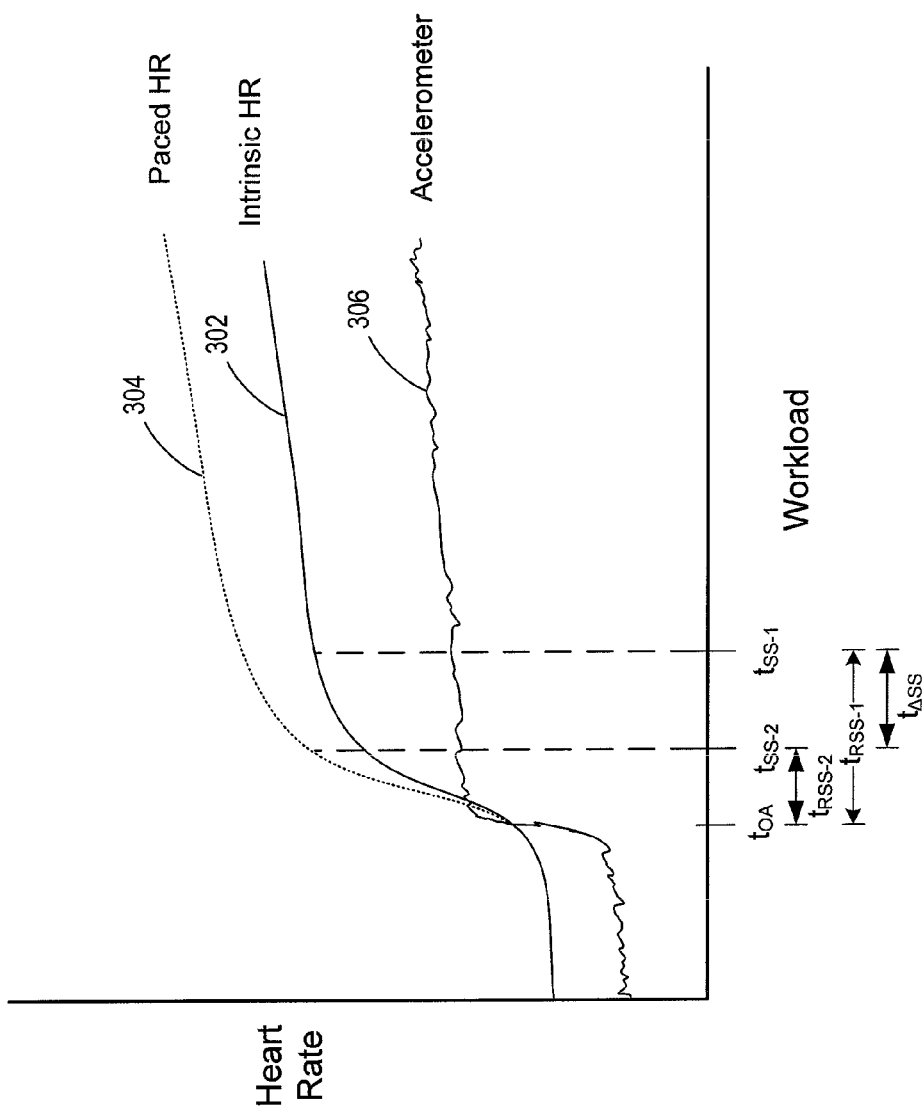
FIG. 3 is a graph showing various aspects of an adaptive rate pacing therapy that improves a patient's mean heart rate response to the onset of activity implemented in accordance with the principles of the present invention.

FIG. 3 is a graph showing various aspects of an adaptive rate pacing therapy that improves a patient's mean heart rate response to the onset of activity implemented in accordance with the principles of the present invention. FIG. 3 shows an accelerometer output signal 306 superimposed on a curve 302 representative of a heart failure patient's intrinsic heart rate 302 at varying workloads. According to embodiments of the present invention, the accelerometer output signal 306 is monitored to determined when a patient becomes active and when patient activity is considered sustained.

For example, a threshold may be established for the accelerometer output signal 306 that discriminates patient activeness that is of interest, such as from exercise, from sleep and wake-rest activities. For example, an accelerometer output signal 306 of less than 15 milli-g may be considered non-activity for purposes of the adaptive rate pacing therapy of the present invention. Accelerometer output signals above 20-25 milli-g are generally indicative of patient activity levels of interest.

A sustained patient activity may be determined based on a minimum period of time during which the patient has been engaged in an activity of interest. For example, a sustained patient activity may be determined if the patient has been engaged in an activity for at least 30 seconds, where that activity is associated with an accelerometer output signal that exceeds a predetermined activity threshold (e.g., >30 mill-g for a minimum of 30 seconds).

Depending on various factors, such as the patient's age, health, and heart failure status, the minimum period of time for declaring that the patient is engaged in a sustained activity may range from about 30 seconds to about 6 minutes. The accelerometer output signal 306 may be averaged or smoothed in order to filter out spurious short periods of below-threshold activity during an otherwise acceptable above-threshold activity. Other techniques may be used to determine if a sustained level of activity has been achieved by the patient. For example, the patient's stroke volume may be measured, and a determination may be made as to whether or not the patient's stroke volume has reached a steady-state value in response to the patient activity (which may take at least about 30-40 seconds or more).

As shown in FIG. 3, accelerometer output signal 306 is below a predetermined activity threshold until time $t_{OA}$, which represents the onset of patient activity. The amplitude of accelerometer output signal 306 increases significantly at time $t_{OA}$, and thereafter increases more slowly, indicating patient engagement in the activity at a sustained intensity. In this illustrative example, time $t_{OA}$ indicates the onset of a qualifying sustained patient activity.

In response to determining that the patient is engaged in a sustained activity at time $t_{OA}$, the patient's intrinsic heart rate signal 302 is evaluated to determine if the patient's heart rate response to the onset of activity is slow. In FIG. 3, the time $t_{SS-1}$ represents the time at which the patient's intrinsic heart rate during the kinetic phase has reached steady-state. The time period $t_{RSS-1}$ represents the duration of time for the patient's intrinsic heart rate during the kinetic phase to reach steady-state as measured from the time $t_{OA}$ (onset of sustained patient activity).

In FIG. 3, it is determined that the patient's intrinsic heart rate response 302 to the onset of patient activity is slow. This determination may be based on the patient's own intrinsic heart rate-to-minute ventilation slope derived from intrinsic heart rate curve 302. One particular approach to making this determination, as will be discussed with reference to FIGS. 4 and 5, involves the development and use of a heart rate response-to-workload profile developed for the patient and accessed during delivery of adaptive rate pacing therapy.

In response to determining that the patient's intrinsic heart rate response 302 to the onset of patient activity is slow, a pacing therapy is delivered to the patient. The pacing therapy increases the patient's heart rate above intrinsic as is shown by paced heart rate signal 304. As can be seen in FIG. 3, the pacing rate is adaptively adjusted to reduce the time of the patient's heart rate response to the onset of activity. This time for the patient's heart rate response to reach steady-state during the activity period in response to the adaptive rate pacing therapy is denote as time $t_{SS-2}$. The time period $t_{RSS-2}$ represents the duration of time for the patient's paced heart rate during the kinetic phase to reach steady-state relative to the time $t_{OA}$. In the illustrative example shown in FIG. 3, the time of the patient's heart rate response to the onset of activity has been reduced by time duration $t_{\Delta SS}$ due to delivery of the adaptive rate pacing therapy.

Figure 4:
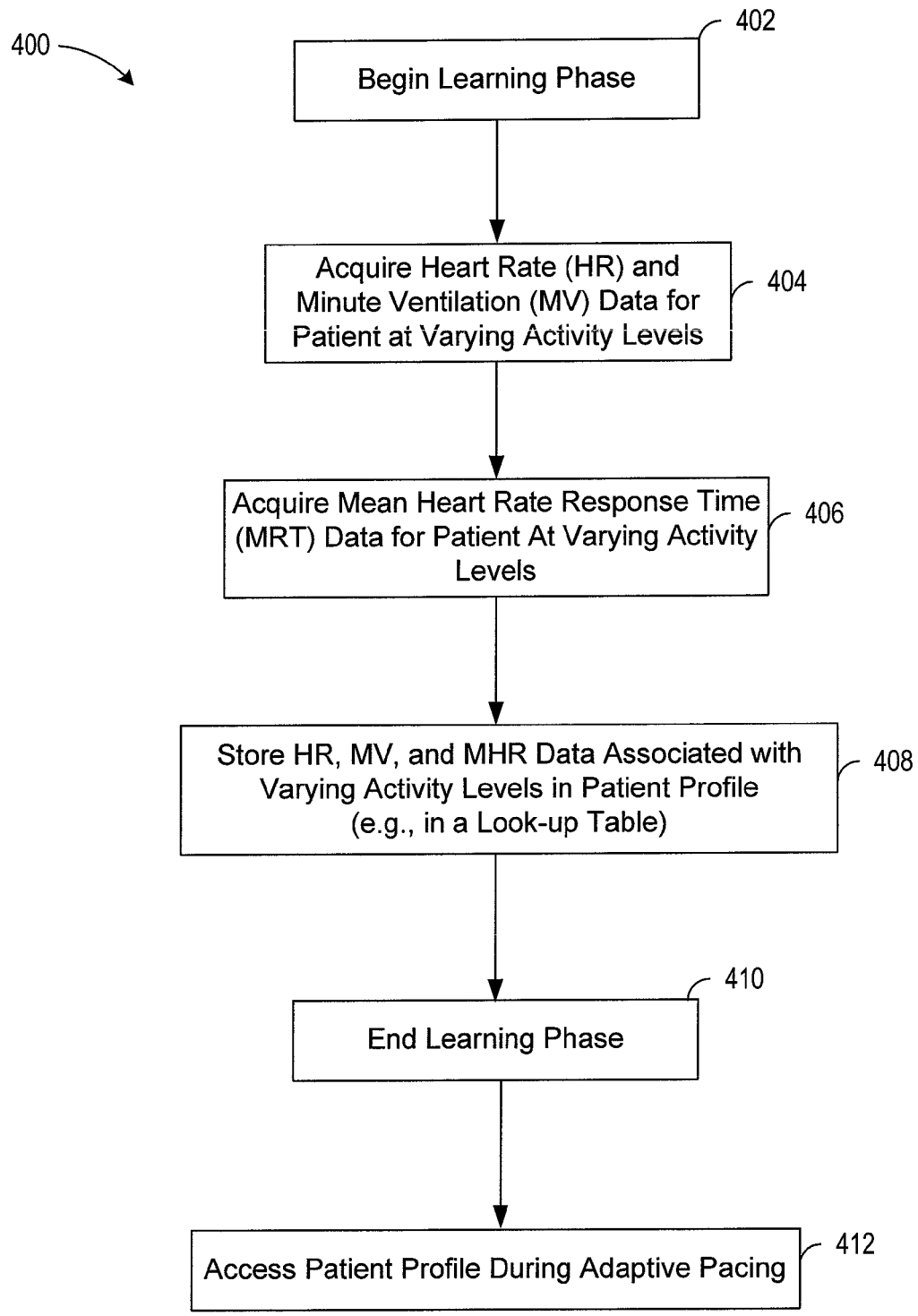
FIG. 4 is a flow diagram of a method for developing a patient profile useful for assessing the status of a heart failure patient in accordance with embodiments of the present invention, and for implementing an adaptive rate pacing therapy for reducing a patient's mean heart rate response to the onset of activity in accordance with other embodiments of the present invention.

Referring now to FIG. 4, there is illustrated a method 400 for developing a patient profile useful for implementing an adaptive rate pacing therapy for reducing a patient's mean heart rate response to the onset of activity in accordance with embodiments of the present invention. According to the method 400 shown in FIG. 4, a learning phase or procedure for developing the patient profile is initiated 402. The learning phase shown in FIG. 4 is preferably performed following implantation of the patient-implantable medical device. The learning phase may be repeated over time as needed. For example, the learning phase shown in FIG. 4 may be invoked in accordance with a schedule or on demand by a clinician. The learning phase may also be repeated when a change in a patient's heart failure status is detected, whether such change is indicative of an improved or worsened status.

The learning phase involves acquiring various physiological and non-physiologic data about the patient. For example, during the learning phase, heart rate (HR) and minute ventilation (MV or VE) data may be acquired 404 for the patient a varying activity levels. In addition, data on the patient's mean heart rate response time (MRT) may be acquired or computed 406 for varying activity levels. These data are preferably acquired during normal day-to-day activities of the patient. As such, the patient need not be subject to special exercises or testing in order to develop the patient profile data, although such may be conducted if desired.

Figure 5:
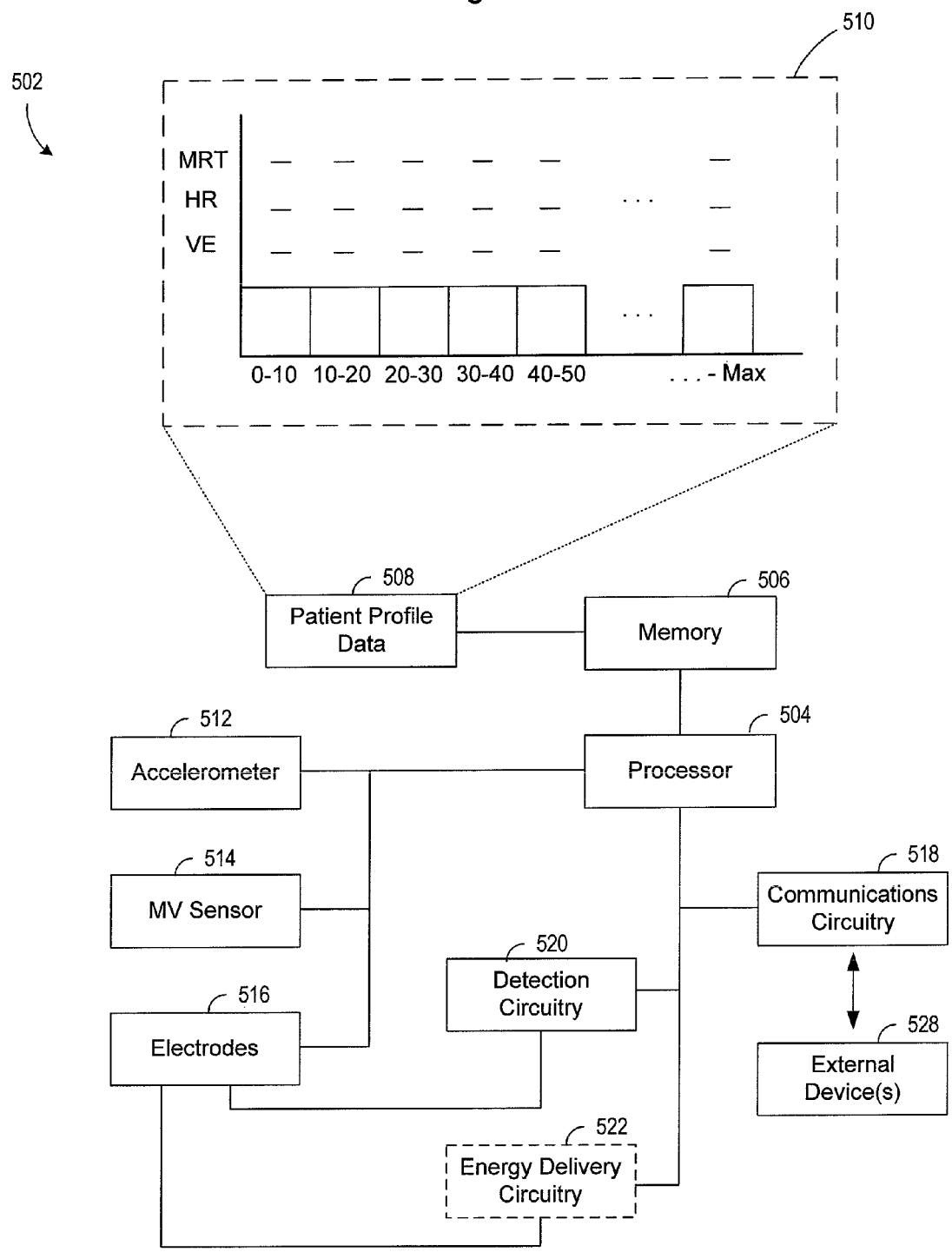
FIG. 5 is a block diagram of a device configured for developing a patient profile useful for assessing the status of a heart failure patient in accordance with embodiments of the present invention, and for implementing an adaptive rate pacing therapy for reducing a patient's mean heart rate response to the onset of activity in accordance with other embodiments of the present invention.

These physiological data and corresponding activity level data are stored 408 in a suitable data structure, such as a look-up table or other array structure. These data may also be stored in the form of mathematical functions derived from curve fitting the data. The data may be organized using a variety of techniques. For example, the data may be acquired and subject to binning, by which HR, VE, and MRT values are associated with ranges of activity levels, expressed in milli-g units for example. An example of this technique is shown in FIG. 5.

According to other approaches, HR, VE, MRT, and activity level values may be grouped using techniques that look for commonality among features within data of interest. For example, clustering may be performed using techniques such as a K-Means clustering algorithm, self-organizing map algorithms, or other data clustering algorithms. It is understood that useful patient profile data need not include all of HR, VE, and MRT parameters, but may include one or two of these parameters (e.g., HR and VE in combination or MRT solely). Moreover, physiological and non-physiological data other than HR, VE, and MRT data may be included in the patient's profile data.

The learning phase may continue until a sufficient amount of data is acquired for a sufficiently wide distribution of patient activity levels, at which time the learning phase may be terminated 410. The learning phase may alternatively be a continuous (or repeatedly invoked) subroutine that continuously updates the patient profile data.

Having established the patient's heart rate response-to-workload profile, this profile data may be accessed 412 during adaptive rate pacing therapy for reducing a patient's mean heart rate response to the onset of activity in accordance with embodiments of the present invention.

FIG. 5 is a block diagram of a device 502 configured to deliver adaptive rate pacing therapy in accordance with embodiments of the present invention. Device 502 may alternatively be configured as a monitor-only device, in which patient profile data and other data (e.g., cardiac activity and/or respiration data) may be acquired.

Device 502 includes a processor 504 coupled to memory 506. Processor 504 is coupled to a number of sensors, including an accelerometer 512 and a physiological sensor, such as a minute ventilation sensor 514. The accelerometer 512 and minute ventilation sensor 514 may be implemented in a known manner. Processor 504 is also coupled to a number of electrodes 516 configured to sense electrical activity of the heart. The electrodes 516 may include one or more (or combinations) of transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Processor 504 is coupled to detection circuitry 520 and energy delivery circuitry 522. Detection circuitry 520 and energy delivery circuitry 522 are respectively coupled to electrodes 516. Detection circuitry 520 is configured to detect cardiac activity and events using known techniques. Energy delivery circuitry 522 is configured to deliver pacing therapies using known techniques. Energy delivery circuitry 522 is also configured to deliver adaptive rate pacing therapies for reducing a patient's mean heart rate response to the onset of activity in accordance with embodiments of the present invention. Energy delivery circuitry 522 may also be configured to deliver high energy cardioversion and defibrillation energy when implemented as an implantable cardioverter/defibrillator (ICD). Energy delivery circuitry 522 may be omitted in devices implemented as monitor-only devices.

Memory 506 may be configured to include or support patent profile data 508. For example, and as shown in FIG. 5, memory 506 may be configured to support a look-up table 510 of binned patent profile data. In this illustrative example, values for MRT, HR, and VE are binned according to their associated activity level values, expressed in terms of milli-g. As shown, a set of MRT, HR, and VE values are associated with activity level ranges of 10 milli-g in width, up to the accelerometer's upper maximum sensitivity limit (typically around 200-250 milli-g). It is understood that the width of the activity level ranges need not be equal, but may vary. The parameters associated with binning may be established automatically (e.g., by the implantable medical device) or by the physician (or a combination of both means).

For example, a given activity level range that has MRT, HR, and VE values that vary widely may be divided into two or more sub-ranges. This division processes may be based on the standard deviation of MRT, HR, and VE values exceeding a preestablished threshold, for example. Varying the width of the activity level ranges may provide for enhanced adaptive rate pacing control, such as by providing for more gradual changes between pacing rate adjustments.

As was discussed previously, an adaptive rate pacing methodology of the present invention may be implemented in a wide variety of implantable medical devices, such as cardiac sensing and/or stimulation devices. For example, various embodiments described herein may be used in connection with devices that provide for heart failure monitoring, diagnosis, and/or therapy. A patient implantable medical device or PIMD of the present invention may incorporate HF features involving dual-chamber or bi-ventricular pacing/therapy, cardiac resynchronization therapy, cardiac function optimization, or other HF related methodologies. For example, a PIMD of the present invention may incorporate features of one or more of the following references: commonly owned U.S. Pat. Nos. 6,411,848; 6,285,907; 4,928,688; 6,459,929; 5,334,222; 6,026,320; 6,371,922; 6,597,951; 6,424,865; 6,542,775; and 7,260 432, each of which is hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of the present invention, are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of the present invention, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference.

A PIMD in accordance with the present invention may implement diagnostic and/or monitoring functions to the exclusion of cardiac stimulation therapy (i.e., monitor-only embodiments). Examples of cardiac monitoring circuitry, structures and functionality, aspects of which may be incorporated in a PIMD of the present invention, are disclosed in commonly owned U.S. Pat. Nos. 5,313,953; 5,388,578; and 5,411,031, which are hereby incorporated herein by reference.

Referring again to FIG. 5, processor 504 is coupled to communications circuitry 518. Communications circuitry 518 may be configured to effect communications between the device of FIG. 5 and one or more external devices 528. External device 528 may be representative of a programmer, a networked patient management system, a portable or hand-held communicator, or other patient-external system. The external device 528 is typically coupled to a user interface, such as a graphical user interface or other interface that provides a display. The user interface preferably includes a user actuatable input/output device, such as a keyboard, touch screen sensor, mouse, light pen, and the like. The user interface may be used by the clinician to make adjustments to parameters of the PIMD, including modifications to the patient's profile data 508, for example.

As was discussed above, A PIMD of the present invention may be implemented to communicate with a patient management server or network via an appropriate communications interface or an external programmer. A PIMD of the present invention may be used within the structure of an advanced patient management (APM) system. The advanced patient management system allows physicians to remotely and automatically monitor cardiac and respiratory functions, as well as other patient conditions. In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 6:
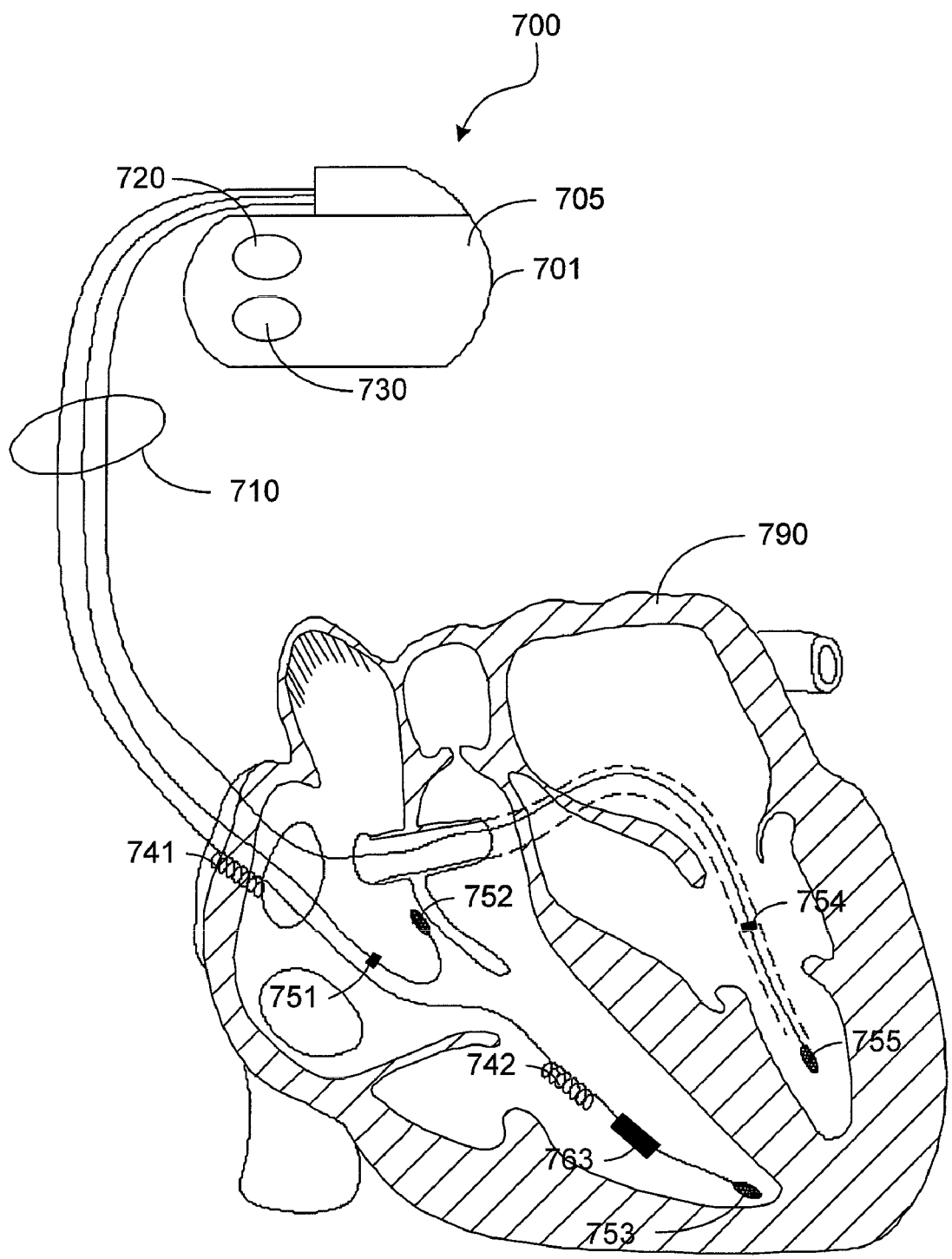
FIG. 6 is an illustration of an implantable cardiac device including a lead assembly shown implanted in a sectional view of a heart, the implantable cardiac device configured to implement methodologies of the present invention.

Referring now to FIG. 6, there is illustrated an embodiment of a PIMD configured to implement methodologies of the present invention. According to one implementation, a PIMD may be configured for monitor-only operation. According to another implementation, a PIMD may be configured to deliver one or both of pacing therapies and cardioversion/defibrillation therapies. Although the following discussion describes various energy delivery aspects, it is understood that these aspects may be excluded in a monitor-only implementation of a PIMD according to the present invention.

In the illustrative implementation shown in FIG. 6, a PIMD includes a cardiac rhythm management device (CRM) 700 including an implantable pulse generator 705 electrically and physically coupled to an intracardiac lead system 710. Portions of the intracardiac lead system 710 are shown inserted into the patient's heart 790. The intracardiac lead system 710 includes one or more electrodes and/or sensors configured to sense electrical cardiac activity of the heart, deliver electrical stimulation to the heart, and sense the patient's transthoracic impedance or transthoracic total impedance. Other sensors may be provided on intracardiac lead system 710, including sensors that measure blood (internal filling) pressure, blood flow, and/or blood temperature, acceleration and/or body acoustics, and/or other physiological parameters. Portions of the housing 701 of the pulse generator 705 may optionally serve as a can electrode.

Communications circuitry is disposed within the housing 701 for facilitating communication between the pulse generator 705 and an external communication device, such as a portable or bed-side communication station, patient-carried/worn communication station (e.g., communicator), external programmer or advanced patient management system interface, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 incorporates an activity detector 720 that may be used to sense patient activity, as well as various respiration and cardiac related conditions. For example, the activity detector 720 may be optionally configured to sense snoring, activity level, and/or chest wall movements associated with respiratory effort, for example. The activity detector 720 is preferably implemented as an accelerometer or other rate sensor positioned in or on the housing 701 of the pulse generator 705. For an activity detector 720 implemented as an accelerometer, the activity detector 720 may also provide respiratory, e.g. rales, coughing, and cardiac, e.g. S1-S4 heart sounds, murmurs, and other acoustic information. An accelerometer may be used to develop respiration waveforms from which various respiratory parameters may be developed.

The lead system 710 and pulse generator 705 of the CRM 700 may incorporate one or more transthoracic impedance sensors that may be used to acquire the patient's respiration waveform, or other respiration-related information. The transthoracic impedance sensor may include, for example, one or more intracardiac electrodes 741, 742, 751-755, 763 positioned in one or more chambers of the heart 790. The intracardiac electrodes 741, 742, 751-755, 763 may be coupled to impedance drive/sense circuitry 730 positioned within the housing of the pulse generator 705.

In one implementation, impedance drive/sense circuitry 730 generates a current that flows through the tissue between an impedance drive electrode 751 and a can electrode on the housing 701 of the pulse generator 705. The voltage at an impedance sense electrode 752 relative to the can electrode changes as the patient's transthoracic impedance changes. The voltage signal developed between the impedance sense electrode 752 and the can electrode is detected by the impedance sense circuitry 730. Other locations and/or combinations of impedance sense and drive electrodes are also possible. The CRM 700 may compute the patient's minute ventilation using known techniques based on the patient's transthoracic impedance changes.

The lead system 710 may include one or more cardiac pace/sense electrodes 751-755 positioned in, on, or about one or more heart chambers for sensing electrical signals from the patient's heart 790 and/or delivering pacing pulses to the heart 790. The intracardiac sense/pace electrodes 751-755, such as those illustrated in FIG. 6, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The lead system 710 may include one or more leads each having one or more electrodes that extend into the heart. FIG. 6 shows three such leads, one that extends into the right atrium, one that extends into the right ventricle, and one that extends into a coronary vein for placement at the surface of the left ventricle. The left ventricular lead, in particular, includes an LV distal electrode 755 and an LV proximal electrode 754 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

The pulse generator 705 may include circuitry for detecting cardiac arrhythmias and/or for controlling pacing or defibrillation therapy in the form of electrical stimulation pulses or shocks delivered to the heart through the lead system 710. The pulse generator 705 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and 6,993,389, which are hereby incorporated herein by reference.

Figure 7:
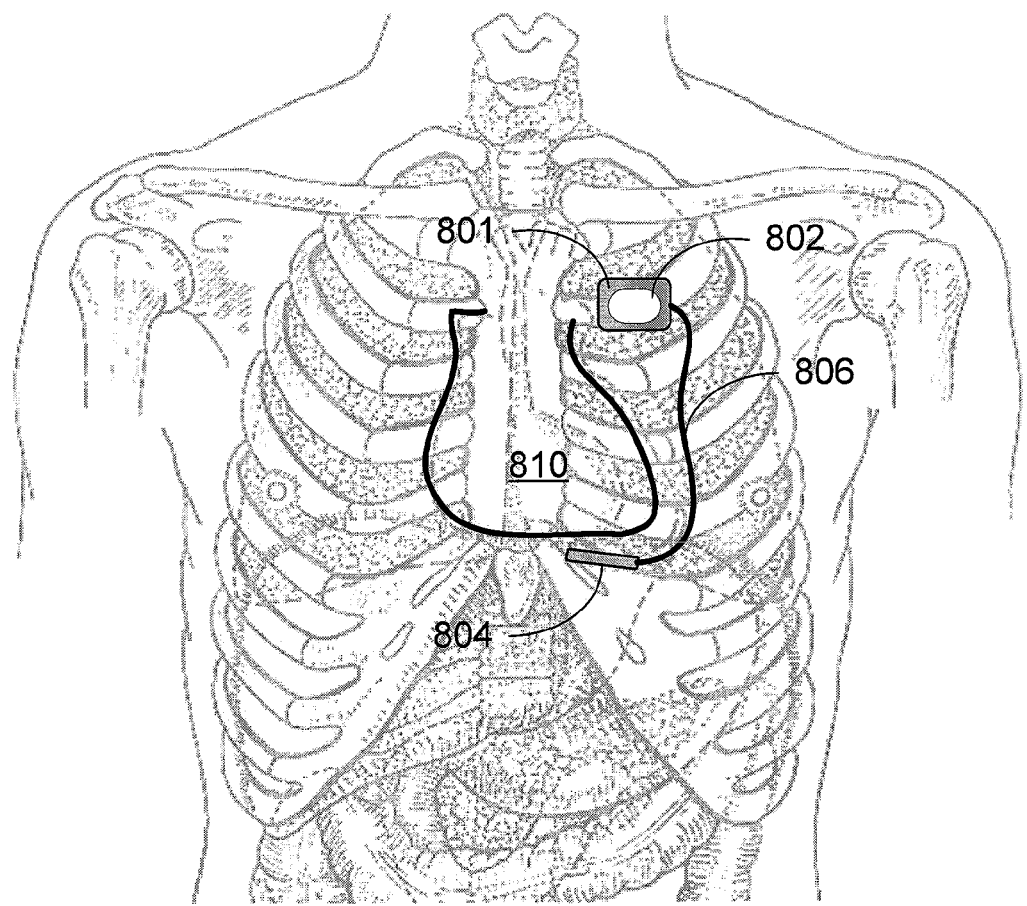
FIG. 7 is an illustration of an implantable medical device including a subcutaneous, non-intrathoracic lead assembly shown implanted outside the ribcage, the implantable medical device configured to implement methodologies of the present invention.

For purposes of illustration, and not of limitation, various embodiments of devices implemented in accordance with the present invention provide for monitor-only operation. FIG. 7 shows an embodiment of a monitor-only PIMD configuration. Such a PIMD may be implanted under the skin in the chest region of a patient. A PIMD may, for example, be implanted subcutaneously such that all or selected elements of the device are positioned on the patient's front, back, side, or other body locations suitable for sensing cardiac activity. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In general, one or more electrodes may be located on the primary housing and/or at other locations about, but not in direct contact with the heart, great vessel or coronary vasculature (such embodiments referred to herein as subcutaneous, non-intrathoracic embodiments).

In a further implementation, for example, one or more electrode subsystems or electrode arrays may be used to sense cardiac activity in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, U.S. Publication No. 2004/0230230 and U.S. Pat. No. 7,499,750, which are hereby incorporated herein by reference.

In one configuration, as is illustrated in FIG. 7, electrode subsystems of a PIMD system are arranged outside the rib cage in relation to a patient's heart 810. The PIMD system includes a first electrode subsystem, comprising a can electrode 802, and a second electrode subsystem 804, coupled to a lead 806, that may include at least two electrodes or at least one multi-element electrode for sensing cardiac electrical activity.

The can electrode 802 is positioned on the housing 801 that encloses the PIMD electronics. In one embodiment, the can electrode 802 includes the entirety of the external surface of housing 801. In other embodiments, various portions of the housing 801 may be electrically isolated from the can electrode 802 or from tissue.

The components, functionality, and structural configurations depicted herein are intended to provide an understanding of various features and combination of features that may be incorporated in a PIMD or patient-external medical device. It is understood that a wide variety of PIMDs, external medical devices, and other implantable cardiac monitoring and/or stimulation device configurations are contemplated, ranging from relatively sophisticated to relatively simple designs. As such, particular medical device configurations may include particular features as described herein, while other such device configurations may exclude particular features described herein.

Various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable device, comprising:
   electrodes for electrically coupling to a patient's heart;
   an activity sensor configured to detect activity of the patient;
   a physiologic sensor configured to measure physiologic demand of the patient;
   memory configured to store patient profile data, the patient profile data comprising heart rate response data relative to varying workloads established for the patient; and
   a processor coupled to the electrodes, activity sensor, physiologic sensor, and memory, the processor configured to determine onset of sustained patient activity and that a heart rate parameter of the patient has reached a steady-state in response to the sustained patient activity, the processor configured to determine a timing relationship between the onset of sustained patient activity and the heart rate parameter reaching the steady-state, and to one or both of initiate and change a pacing therapy based on a comparison of the timing relationship to a stored patient profile of the patient's heart rate response to varying workloads indicating slow heart rate response to the sustained patient activity.

2. The device of claim 1, wherein the processor is configured to withhold the pacing therapy in response to the processor determining that the patient's heart rate response to the sustained activity is not slow.

3. The device of claim 1, wherein the processor is configured to determine sustaining of the patient activity in response to sensing an output signal produced by the activity sensor indicative of sustained patient activity for a time duration exceeding a threshold ranging between about 30 seconds and about 6 minutes.

4. The device of claim 1, wherein the processor is configured to determine sustaining of the patient activity in response the patient's stroke volume reaching a steady-state value in response to the activity.

5. The device of claim 1, wherein the processor is configured to determine sustaining of the patient activity in response to sensing an output signal produced by the activity sensor and the physiologic sensor, respectively.

6. The device of claim 1, wherein the activity sensor comprises an accelerometer and the physiologic sensor comprises a minute ventilation sensor or a pressure sensor.

7. The device of claim 1, wherein the processor is configured to adjust an upper rate limit of the pacing therapy based on the patient's profile.

8. The device of claim 1, wherein the processor is configured to adjust one or both of an AV delay parameter and a VV delay parameter of the pacing therapy.

9. The device of claim 1, wherein the processor is configured to acquire patient profile data comprising one or both of the patient's intrinsic heart rate and minute ventilation, and to store the patient profile data in the memory.

10. The device of claim 1, wherein the processor is configured to acquire patient profile data comprising mean heart rate response time data at varying activity levels, and to store the patient profile data in the memory.

11. The device of claim 1, wherein the processor determines slowness of the patient's heart rate response based on patient profile data associated with an activity level of the profile corresponding to the patient's actual activity level.

12. An implantable device, comprising:
electrodes for electrically coupling to a patient's heart;
an activity sensor configured to detect activity of the patient;
a physiologic sensor configured to measure physiologic demand of the patient;
memory configured to store patient profile data, the patient profile data comprising heart rate response data relative to varying workloads established for the patient; and
a processor coupled to the electrodes, activity sensor, physiologic sensor, and memory, the processor configured to determine onset of sustained patient activity and whether the patient's intrinsic heart rate response is slow during a kinetic phase of the onset of the sustained activity based on a timing relationship between the onset of sustained patient activity and a heart rate parameter reaching the steady-state in response to the sustained patient activity, the processor configured to initiate or change a pacing therapy to deliver pacing pulses at a rate above the patient's intrinsic heart rate based at least in part on the patient profile data if the patient's intrinsic heart rate response during the kinetic phase is determined by the processor to be slow.

13. The device of claim 12, wherein the processor is configured to initiate or change the pacing therapy to deliver pacing pulses at a rate sufficient to improve a chronotropic response of the patient to the sustained activity.

14. The device of claim 12, wherein the processor is configured to initiate or change the pacing therapy to deliver pacing pulses at a rate sufficient to improve a chronotropic response of the patient to the sustained activity without overpacing the patient.

15. The device of claim 12, wherein the processor is configured to initiate or change the pacing therapy to deliver pacing pulses at a rate that improves a patient's chronotropic response of the patient at different levels of patient activity.

16. The device of claim 12, wherein the processor is configured to initiate or change the pacing therapy to deliver pacing pulses at a rate sufficient to increase the patient's heart rate response for reaching a steady-state exercise level of the sustained activity.

17. The device of claim 12, wherein the processor is configured to determine onset of sustained patient activity by sensing that the patient has been active for a time duration exceeding a threshold ranging between about 30 seconds and about 6 minutes.

18. The device of claim 12, wherein the processor is configured to determine onset of sustained patient activity by sensing that the patient's stroke volume has reached a steady-state value in response to the patient activity.

19. The device of claim 12, wherein the processor is configured adjust one or both of an AV delay parameter and a VV parameter of the pacing therapy to deliver pacing pulses at the rate above the patient's intrinsic heart rate.

20. An implantable device, comprising:
means for determining onset of sustained patient activity;
means for determining that a heart rate parameter of the patient has reached a steady-state in response to the sustained patient activity;
means for determining a timing relationship between the onset of sustained patient activity and the heart rate parameter reaching the steady-state; and
means for one or both of initiating and changing a pacing therapy based on a comparison of the timing relationship to a profile of the patient's heart rate response to varying workloads indicating slow heart rate response to the sustained patient activity.

* * * * *